United States Patent [19]

Youm et al.

[11] 4,229,841
[45] Oct. 28, 1980

[54] WRIST PROSTHESIS

[75] Inventors: Youngil Youm, Beltsville, Md.; Adrian E. Flatt, Iowa City, Iowa

[73] Assignee: The University of Iowa Research Foundation, Iowa City, Iowa

[21] Appl. No.: 961,821

[22] Filed: Nov. 17, 1978

[51] Int. Cl.³ .............................................. A61F 1/24
[52] U.S. Cl. ..................................... 3/1.91; 128/92 C
[58] Field of Search .................. 3/1.91, 1.9; 128/92 C

[56] References Cited

U.S. PATENT DOCUMENTS

| 4,040,130 | 8/1977 | Laure | 3/1.91 |
| 4,063,314 | 12/1977 | Loda | 3/1.91 |

FOREIGN PATENT DOCUMENTS 526355  9/1976  U.S.S.R. ..................................... 3/1.91

Primary Examiner—Ronald L. Frinks
Attorney, Agent, or Firm—Beveridge, DeGrandi, Kline & Lunsford

[57] ABSTRACT

A proximal component affixed to the radius of the forearm and a distal component affixed to the hand are connected by a joint which prevents axial rotation between the components relative to the forearm axis and provides relative movement of the components about two substantially perpendicular axes which are transverse to the forearm axis for radial-ulnar hand movement and flexion-extension hand movement.

14 Claims, 3 Drawing Figures

WRIST PROSTHESIS

This invention is related to a project performed under National Institutes of Health Grant No. AM 14659.

BACKGROUND AND SUMMARY

This invention relates to a total wrist prosthesis designed for surgical replacement of the wrist joints in patients such as those suffering from rheumatoid degenerative and traumatic arthritis, and similar conditions.

Surgical replacements of human joints have been successfully achieved in recent years, particularly for the finger and hip joints. Although there is a recognized need for a total wrist joint replacement, no device fully effective for this purpose has been available. The few known wrist prostheses are basically simple ball and socket structures which provide unconstrained freedom of movement in all planes which intersect the center of the ball. Clinical trials have shown that such freedom of movement may lead to a permanently deformed position of the wrist which substantially limits its motion.

One existing prosthesis, called a Meuli prosthesis, includes a three-part ball and socket and is provided with intramedullary stems for methylmethacrylate fixation in the radius and metacarpal bones. The distal component is provided with a socket and intramedullary stems for the second and third metacarpals. A ball located between the metacarpal stems is manufactured either with or without a neck. Mechanically, the Meuli prosthesis provides equal ranges of motion for both radial-ulnar deviation and flexion-extension motion. The ball and socket design permits unwanted axial rotation when torque is applied to the hand around the forearm axis. The stability of the Meuli prosthesis depends entirely on the tendons and surrounding soft tissues, with the wrist tendons being relied upon to apply a proper tension to maintain the prosthesis at a suitable resting position. Bending of the stems of this prosthesis is generally required prior to implantation to offset the center of rotation from the axis of the radial stem and radius. The absence of such an offset is considered undesirable according to the article "Total Wrist Arthroplasty: A Preliminary Report." The Journal of Hand Surgery, Vol. 2, No. 5, 1977, pp. 337-344, by R. D. Beckenbaugh and R. L. Linscheid.

Another wrist prosthesis is the Loda prosthesis made in Argentina. It has a distal component, a cylindrical socket component with a spherical ball-receiving recess, and a proximal metallic component which includes a stem received in the intramedullary canal of the radius. The distal component includes a single intramedullary pin and is provided with antirotary flaps which prevent its rotation relative to the metacarpal bone. The socket component is affixed to the proximal component at a location which offsets the center of rotation from the axis of the radial stem. As in the Meuli prosthesis, the range of motion of the Loda prosthesis is the same in all directions and the prosthesis permits rotation of the distal component about the forearm axis if torque is applied to the hand. The Loda prosthesis has more stability but less range of motion than the Meuli prosthesis. It also has more constraint in the ball and socket joint. However, laboratory tests have shown that at extreme hand positions, the rim of the cylindrical socket acts as a fulcrum which can lead to dislocation of the ball and socket when a small load is applied at the end of the hand.

A third wrist prosthesis, known as the Volz prosthesis, is an unconstrained two piece device formed of a proximal component and a distal component formed respectively of ultra-high molecular weight polyethylene and Vitallium alloy. Its reported ranges of motion are 90° in flexion-extension movement and 50° in radial-ulnar deviation. A 1976 report on this prosthesis described seventeen cases of clinical results. This prosthesis has not been tested by the present inventors, but its description suggests that its center of rotation is aligned with the radius stem axis. This is undesirable as previously mentioned. Also, due to the unconstrained joint construction of the Volz prosthesis, it has little stability.

The present invention is believed to surpass prior wrist prostheses in its resemblance to the characteristics of a normal human wrist. The normal wrist joint, formed of eight carpal bones arranged in a distal row and a proximal row, is dynamically balanced by muscle forces, ligament forces, bony contact forces, and the viscoelastic forces of the surrounding soft tissue. It is a biaxial joint with two degrees of freedom which provide flexion-extension motion and radial-ulnar deviation. Flexion-extension motion occurs at the intercarpal and radiocarpal joints simultaneously, the range of such motion being approximately 80° from neutral to flexion and 70° from neutral to extension. In radial-ulnar deviation, the neutral-to-radial motion occurs mainly between the distal and proximal carpal rows, the proximal row of carpal bones remaining stationary. During neutral-to-ulnar deviation, there are intercarpal and radiocarpal joint motions which cumulatively provide an ulnar deviation which is larger than the radial deviation.

The center of normal radial-ulnar rotation in a dorsal or PA x-ray view is offset from the forearm axis towards the radius one-twelfth of the total width of the radius and ulna. It is also offset ulnaward from the radius axis a distance which is about one-tenth of the length of the third metacarpal. The total width of the radius and ulna is the distance from the ulnar border of the ulna to the radial border of the radius, measured perpendicular to the ulna axis at any point in the distal one-third of the radial and ulnar diaphyses. The center of flexion-extension rotation, seen in a lateral x-ray view, is displaced volarward from the radius axis a distance which is about 10% of the third metacarpal length.

The prosthesis of this invention includes a proximal component and a distal component, which are provided with means for connecting them respectively to the forearm and metacarpal bones. Means are provided for connecting the proximal component to the distal component to prevent axial rotation between the components relative to the forearm axis and to provide pivotal movement of the distal component relative to the proximal component, such movement being about two substantially perpendicular axes which are transverse to the forearm axis for radial-ulnar hand movement and flexion-extension hand movement. The pivot axis for radial-ulnar hand movement is preferably located at a position laterally offset ulnaward from the radius stem axis when the connector means is implanted in the lower forearm. Preferably, the distal component is connected to the metacarpal bones by means of a pair of diverging intramedullary stems which are stationary with respect to each other for engagement in the second and third metacarpal bones.

THE DRAWINGS

DESCRIPTION OF A PREFERRED EMBODIMENT

Figure 1:
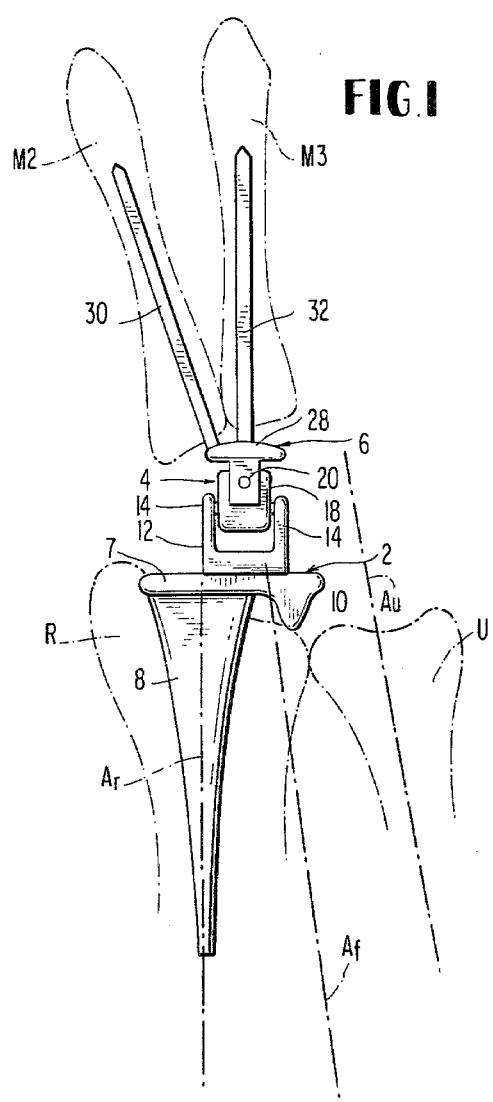
FIG. 1 is a dorsal view of a prosthesis constructed according to the invention, showing its relationship to the bones and axes of the hand and forearm.

The prosthesis includes a proximal component 2, a joint component 4 and a distal component 6. It is designed so that a single prosthesis may be used for either the right hand or the left hand. The proximal component 2 has a base 7 with a depending intramedullary radius stem 8 of elliptical cross-section and a depending projection 10 which provides a shoulder resting on and engaging the end of the radius R at a location spaced laterally ulnaward from the axis $A_r$ of stem 8. The projection 10 lends some support to the base 7 when compressive forces are applied, and it helps resist rotation of the stem 8 about the radius axis $A_r$. A U-shaped bracket 12 has a base immovably fastened to the proximal surface of the base 7 and a pair of spaced upstanding flanges 14 which are apertured to receive a pivot pin 16 shown in FIG. 2.

Figure 3:
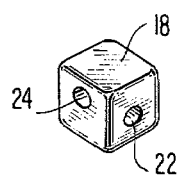
FIG. 3 is a perspective view of the movable joint member of the prosthesis.

The joint component includes a solid inflexible plastic member 18 best shown in FIG. 3 and pivot pins 16 and 20 which are received in mutually perpendicular bores in the member 18. These bores are designated 22 and 24 in FIG. 3. Pin 16 is received by bore 22 and oriented to provide movement of elements 6 and 18 about a pivot axis for flexion-extension hand movement. The pivot pin 20 lies in bore 24 to connect the member 18 to the distal component 6, enabling the distal component to pivot about an axis for radial-ulnar deviation. This axis is not aligned with the axis $A_r$ of the radius and radius stem 8, but is offset therefrom in a direction toward the ulna U. The joint elements 16, 18 and 20 prevent axial rotation between components 2 and 6 relative to the forearm axis $A_f$, the latter being a line drawn equidistant from the radial border and the ulnar border in a PA X-ray view.

The distal component 6 includes a U-shaped bracket 28 which carries a pair of diverging intramedullary stems 30 and 32 which are formed of ductile metal and designed for implantation in the second and third metacarpal bones M2 and M3. In the lateral view, the axes of stems 30 and 32 are aligned with the axis of radius stem 8. The bracket 28 includes a pair of flanges 34 and 36 which lie on opposite sides of the joint member 18 and are apertured to receive the pivot pin 20. As previously mentioned, the pivot pin 20 is offset ulnaward from the axis of the radial stem 8 to provide for nearly normal radial-ulnar movement of the hand.

Both of the pivot pins 16 and 20 are retained in their illustrated positions by threaded connections, lock springs seated in external grooves on the respective pins, or by permanent fixation. During surgical implantation, the proximal and distal components 2 and 6 are not connected together by the joint component 4 until the intramedullary stems are fixed to the respective bones, so one of the pin-retaining means should be capable of being engaged during the surgical procedure.

Figure 2:
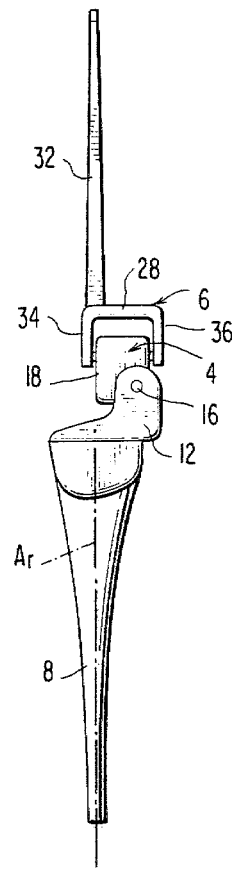
FIG. 2 is a lateral view of the prosthesis, with the dorsal side on the left and the volar side on the right.

In determining the appropriate size and configuration of a prosthesis for a patient, the length of the third metacarpal M3 provides a basis for calculation. The carpal height, i.e. the distance in the dorsal view from the base of the third metacarpal to the distal subchondral plate of the radius should be about 51–57% of the length of the third metacarpal. The carpal ulnar distance, i.e. the perpendicular distance in the dorsal view from the center of pin 20 to the lateral projection of the longitudinal axis $A_u$ of the ulna, is about 27–33% of the length of the third metacarpal. The axis of pin 20 is also offset from the radius axis $A_r$ a distance which is about one-twelfth of the total width of the radius and ulna or about one-fifth to one-sixth the distance component measured parallel to the axis $A_r$ between the proximal surface of base 7 and the distal surface of bracket 28. The axis of pin 16 is offset volarward from the axis of stem 8 as shown in FIG. 2. This causes the carpal volar distance, i.e. the perpendicular distance in a volar direction from the radius axis $A_r$ to the center of flexion-extension rotation in lateral view, to be about 10% of the length of the third metacarpal.

The prosthetic joint of this invention is installed by a surgical procedure which involves the fixation of the radial stem 8 to the radius R by conventional fixation techniques such as those using a methylmethacrylate composition. The stems 30 and 32 are similarly affixed to the metacarpal bones M3 and M3, and the joint connection is made by installing one of the pivot pins 16 or 20, the other pivot pin having previously been installed and retained in the illustrated position. The joint when implanted is an improved, stable pain-free prosthesis. It provides for hand movement resembling that of a normal wrist joint and, unlike prior wrist prostheses, it prevents axial rotation of the hand relative to the forearm axis $A_f$.

Although a preferred embodiment of the invention has been illustrated and described, it will be apparent to persons in the field of this invention that it may take a variety of different forms. Therefore, it is emphasized that the invention is not limited to the single disclosed embodiment but is embracing of a wide variety of devices which fall within the spirit of the following claims.

We claim:

1. A wrist prosthesis comprising,
   a proximal component, means for connecting the proximal component to the radius of the forearm,
   a distal component, means for connecting the distal component to at least one of the metacarpal bones,
   joint means for connecting the proximal component to the distal component to prevent axial rotation between said components relative to the forearm axis and to provide movement of said distal component relative to said proximal component about two substantially perpendicular axes which are transverse to the forearm axis for radial-ulnar hand movement and flexion-extension hand movement
   said joint means including a joint member, a first pivot pin defining a first pivot axis connected to the joint member and to one said component to provide flexion-extension movement of the hand about said first pivot axis, a second pivot pin defining a second pivot axis connected to the joint member and to the other said component to provide radial-ulnar deviation of the hand about said second pivot axis.

2. The wrist prosthesis of claim 1 wherein the means for connecting the proximal component to the radius of the forearm includes an intramedullary stem, and the means for connecting the distal component to at least one of the metacarpal bones includes an intramedullary stem.

3. The wrist prosthesis of claim 1 wherein the proximal component includes an intramedullary stem for connecting the proximal component to the radius, said proximal component also having a shoulder for engaging the end of the radius at a location spaced laterally ulnaward from the axis of the intramedullary stem.

4. The wrist prosthesis of claim 1 wherein said first pivot axis is closer than said second pivot axis to said proximal component.

5. The wrist prosthesis of claim 1 wherein the proximal component includes an intramedullary stem for connecting the proximal component to the radius, said axis of the joint means providing radial-ulnar movement being laterally offset ulnaward from the axis of the intramedullary stem.

6. The wrist prosthesis of claim 5 in which said proximal component has a shoulder for engaging the end of the radius at a location spaced laterally ulnaward from the axis of the intramedullary stem.

7. The wrist prosthesis of claim 1 wherein the proximal component includes an intramedullary stem for connecting the proximal component to the radius of the forearm, said axis of the joint means which provides flexion-extension movement being offset volarward from the axis of said intramedullary stem.

8. The wrist prosthesis of claim 7 wherein the axis of the joint means providing radial-ulnar movement is laterally offset ulnaward from the axis of the intramedullary stem.

9. A wrist prosthesis comprising,
a proximal component, a distal component, and a joint member,
connector means for connecting the proximal component to the radius of the forearm,
a first pivot pin defining a first generally transverse pivot axis connected to said proximal component and said joint member to provide pivotal movement of the joint member about said first generally transverse pivot axis,
connector means for connecting the distal component to at least one of the metacarpal bones,
a second pivot pin defining a second generally transverse pivot axis connected to said distal component and said joint member to provide pivotal movement of said distal component about said second generally transverse pivot axis which is generally perpendicular to said first pivot axis,
said pivot pins being oriented to provide radial-ulnar movement and flexion-extension hand movement and to prevent axial rotation of the distal component relative to the proximal component.

10. The wrist prosthesis of claim 9 wherein said means for connecting said proximal component to the radius of the forearm includes an intramedullary stem, said pivot pin providing radial-ulnar hand movement being laterally offset from the axis of said intramedullary stem.

11. The wrist prosthesis of claim 10 wherein said pivot pin providing flexion-extension hand movement is offset volarward from the axis of said intramedullary stem.

12. The wrist prosthesis of claim 9 wherein the first pivot pin is oriented to provide flexion-extension hand movement and the second pivot pin is oriented to provide radial-ulnar hand movement.

13. The wrist prosthesis of claim 9 wherein said means for connecting said proximal component to the radius of the forearm includes an intramedullary stem, which has an axis offset volarward from said pivot axis providing flexion-extension hand movement being offset volarward from the axis of said intramedullary stem.

14. The wrist prosthesis of claim 9 wherein said connector means on said distal component includes a pair of diverging intramedullary pins which are stationary with respect to each other for engagement in the second and third metacarpal bones.

* * * * *